(12) United States Patent
Miller et al.

(10) Patent No.: US 7,292,349 B2
(45) Date of Patent: Nov. 6, 2007

(54) METHOD FOR BIOMOLECULAR SENSING AND SYSTEM THEREOF

(75) Inventors: Benjamin Miller, Rochester, NY (US); Lewis Rothberg, Pittsford, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 10/282,274

(22) Filed: Oct. 28, 2002

(65) Prior Publication Data

US 2003/0112446 A1   Jun. 19, 2003

Related U.S. Application Data

(60) Provisional application No. 60/339,255, filed on Oct. 26, 2001.

(51) Int. Cl.
*G01B 9/02* (2006.01)
(52) U.S. Cl. .................................... 356/504; 356/632
(58) Field of Classification Search ............... 356/450, 356/491, 492, 493, 495, 503, 504, 517, 451, 356/632, 630
See application file for complete search history.

(56) References Cited

U.S. PATENT DOCUMENTS

| | | | |
|---|---|---|---|
| 3,612,692 A | 10/1971 | Kurppa et al. | |
| 4,521,522 A | 6/1985 | Lundström et al. | |
| 4,606,638 A * | 8/1986 | Sommargren | 356/492 |
| 4,857,273 A | 8/1989 | Stewart | |
| RE33,581 E | 4/1991 | Nicoli et al. | |
| 5,089,387 A | 2/1992 | Tsay et al. | |
| 5,482,830 A | 1/1996 | Bogart et al. | |
| 5,491,556 A | 2/1996 | Stewart et al. | |
| 5,494,829 A | 2/1996 | Sandstrom et al. | |
| 5,541,057 A | 7/1996 | Bogart et al. | |
| 5,550,063 A | 8/1996 | Bogart | |
| 5,552,272 A | 9/1996 | Bogart | |
| 5,563,707 A * | 10/1996 | Prass et al. | 356/517 |
| 5,629,214 A | 5/1997 | Crosby | |
| 5,631,171 A | 5/1997 | Sandstrom et al. | |

(Continued)

FOREIGN PATENT DOCUMENTS

WO   WO91/04491   4/1991

(Continued)

OTHER PUBLICATIONS

Ostroff, R., Hopkins, D., Haeberli, A.B., Baouchi, W., and Polisky, B., "Thin Film Biosensor For Rapid Visual Detection Of Nucleic Acid Targets," *Clinical Chemistry* 45:1659-1664 (1999).

(Continued)

*Primary Examiner*—Hwa (Andrew) Lee
(74) *Attorney, Agent, or Firm*—Nixon Peabody LLP

(57) ABSTRACT

A sensing system and method for biomolecular sensing. The system includes: a receptor for the at least one target, the receptor including a substrate and a transparent coating on the substrate having front and back surfaces; a light source positioned to direct at least a portion of light from the light source toward the coating on the receptor; and a detector positioned to capture the light reflected from the front and back surfaces of the coating, the detector identifying presence of at least one target based on a change in the interference pattern of captured light.

26 Claims, 16 Drawing Sheets

U.S. PATENT DOCUMENTS

| | | |
|---|---|---|
| 5,633,724 A | 5/1997 | King et al. |
| 5,639,671 A | 6/1997 | Bogart et al. |
| 5,869,272 A | 2/1999 | Bogart et al. |
| 5,955,377 A | 9/1999 | Maul et al. |
| 6,060,237 A | 5/2000 | Nygren et al. |
| 6,166,818 A | 12/2000 | Nagano et al. |
| 6,218,194 B1 | 4/2001 | Lyndin et al. |
| 6,225,625 B1 | 5/2001 | Pirrung et al. |
| 6,277,330 B1 | 8/2001 | Liu et al. |
| 6,277,653 B1 * | 8/2001 | Challener et al. ............ 436/518 |
| 6,411,388 B1 * | 6/2002 | Downer et al. ............. 356/451 |
| 6,483,585 B1 | 11/2002 | Yang |
| 6,498,335 B2 | 12/2002 | Modlin et al. |
| 6,714,303 B2 | 3/2004 | Ivarsson |
| 6,720,177 B2 | 4/2004 | Ghadiri et al. |
| 2001/0029050 A1 | 10/2001 | Starzl et al. |
| 2003/0205681 A1 | 11/2003 | Modlin |

FOREIGN PATENT DOCUMENTS

| | | |
|---|---|---|
| WO | WO 02/093145 A1 | 11/2002 |
| WO | WO 03/064995 A2 | 8/2003 |
| WO | WO 03/065041 A1 | 8/2003 |

OTHER PUBLICATIONS

Jenison, R., Yang, S., Haeberli, A., and Polisky, B., "Interference-Based Detection Of Nucleic Acid Targets On Optically Coated Silicon," *Nature Biotechnology* 19:62-65 (2001).

* cited by examiner

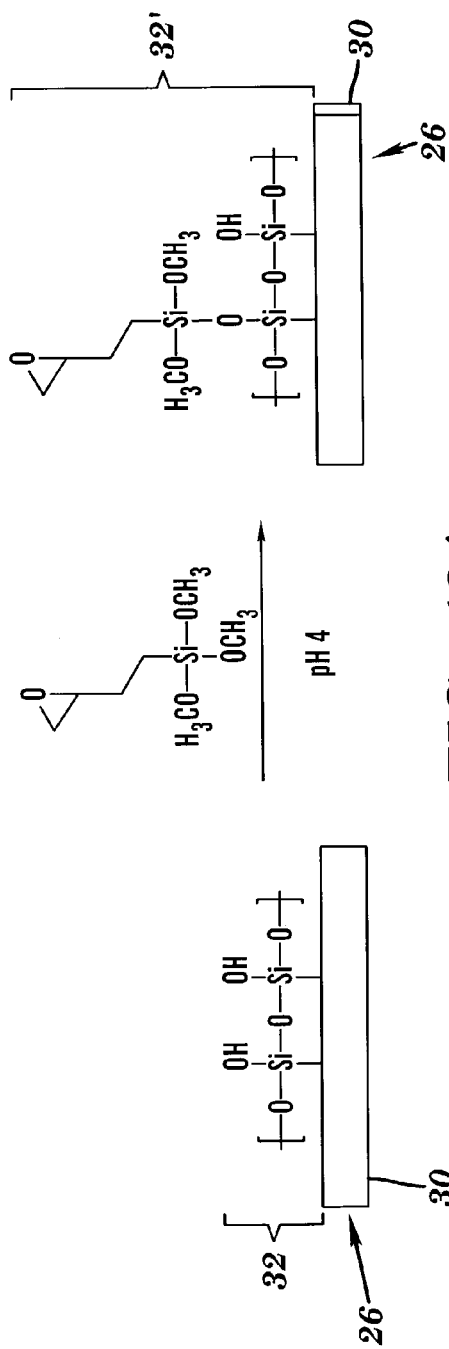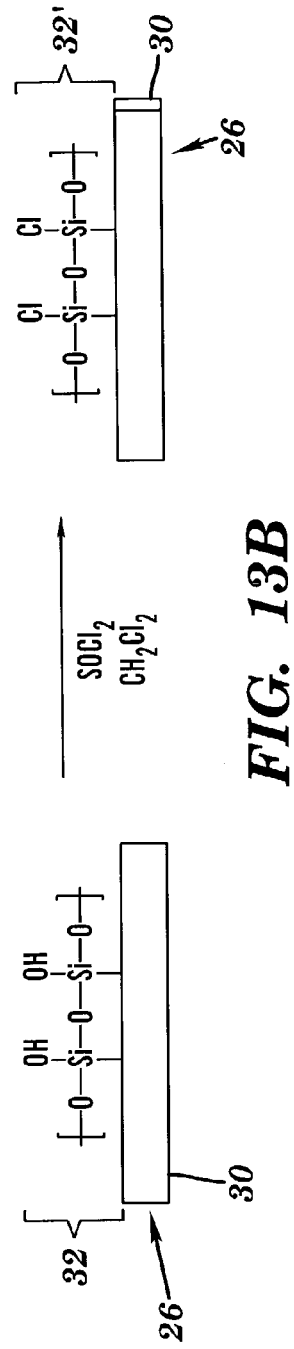
FIG. 13A
FIG. 13B

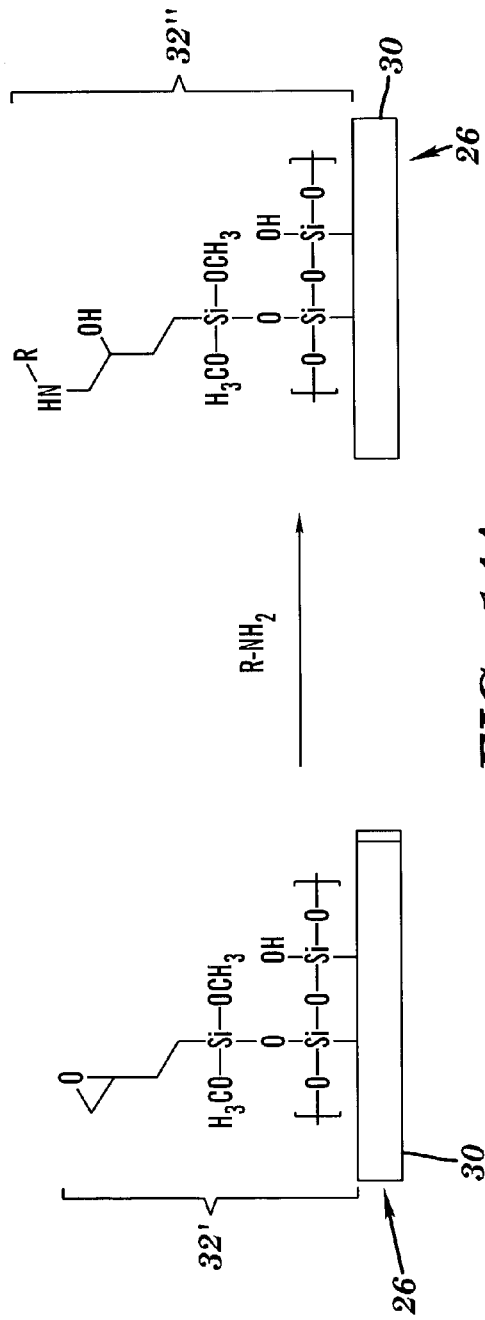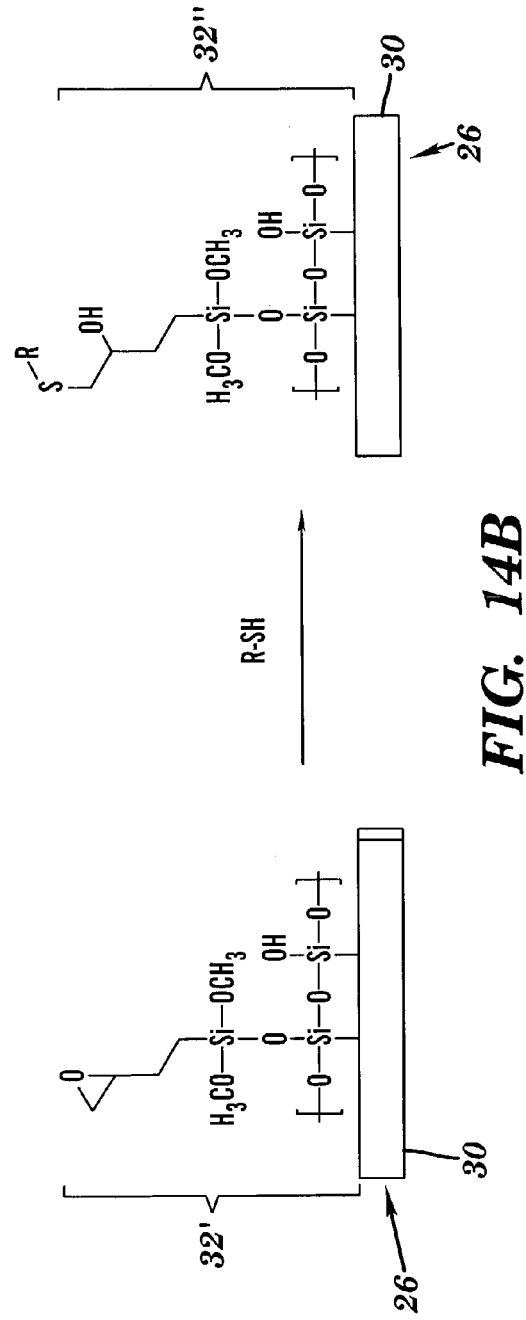
FIG. 14A
FIG. 14B

METHOD FOR BIOMOLECULAR SENSING AND SYSTEM THEREOF

The present invention claims the benefit of U.S. Provisional Patent Application Ser. No. 60/339,255, filed Oct. 26, 2001, which is hereby incorporated by reference in its entirety.

FIELD OF THE INVENTION

This invention relates to a method for biomolecular sensing and a system thereof.

BACKGROUND OF THE INVENTION

Microarraying and biological sensing are important emerging technologies with huge potential impact on clinical and research medicine. Present methodologies for microarraying and biological sensing are based on fluorescence, radioactive, colorimetry, or surface plasmon resonance assays of molecular recognition chemistry with the former garnering the most attention.

Although these methodologies work, there are problems with each of them. Fluorescence and radioactivity require a special tagging chemistry and thus are time-consuming and cumbersome to use. Additionally, methodologies based on radiation are hard to scale to arrays, and have associated safety and environmental problems. Colorimetry requires chemical amplification when there are large changes in the thickness of the coating and thus is very complicated to adapt to arraying.

The present invention is directed to overcoming these and other deficiencies in the art.

SUMMARY OF THE INVENTION

A sensing system in accordance with one embodiment of the present invention includes: a receptor for the at least one target, the receptor including a substrate and translucent coating on the substrate having front and back surfaces; a light source positioned to direct at least a portion of light from the light source toward the coating on the receptor in a manner effective to result in a condition of near perfect interference; and a detector positioned to measure the light reflected from the front and back surfaces of the coating and identifying presence of at least one target based on the measured reflected light.

A method for biomolecular sensing in accordance with another embodiment of the present invention includes: providing a receptor for the at least one target, the receptor including a substrate and a translucent coating on the substrate having front and back surfaces; directing a light at the front and back surfaces of the coating on the receptor in a manner effective to result in a condition of near perfect interference; measuring the light reflected from the front and back surfaces of the coating on the receptor; and providing an output identifying the at least one target based on the measured reflected light.

The present invention provides a system and method for detecting molecular adsorption based on simple reflectivity. One advantage of this reflective technique is that it works without any special tagging chemistry as is required for fluorescence or radioactivity. Additionally, the present invention has a high degree of sensitivity and can determine the precise amount of absorption of a target in a sample. Further, the present invention can be easily adapted to arraying on a large scale and can be done in situ under standard aqueous biological media. The present invention also scales favorably with the size of adsorbate so that it should be extraordinarily sensitive to large systems, such as cells that have been selectively bound using cell membrane markers.

BRIEF DESCRIPTION OF THE DRAWINGS

FIGS. 13A-B illustrate silanization (13A) and halide (13B) coupling agents which can be attached, e.g., to a silicon dioxide coated receptor and used to covalently bind adsorbates (for purposes of illustration, trimethoxy(3-oxiranylpropyl)silane is shown); and FIGS. 14A-E illustrate the attachment schemes for binding adsorbates R—NH2, R—SH, and R—OH upon opening of the epoxide group on the coupling agent (14A-C, respectively); adsorbate R-alkenyl to the alkenyl group on the coupling agent (14D); and adsorbate R—OH upon displacement of a halide coupling agent (14E). For purposes of illustration, trimethoxy(3-oxiranylpropyl)silane is illustrated in FIGS. 14A-C.

DETAILED DESCRIPTION OF THE INVENTION

Figure 1:
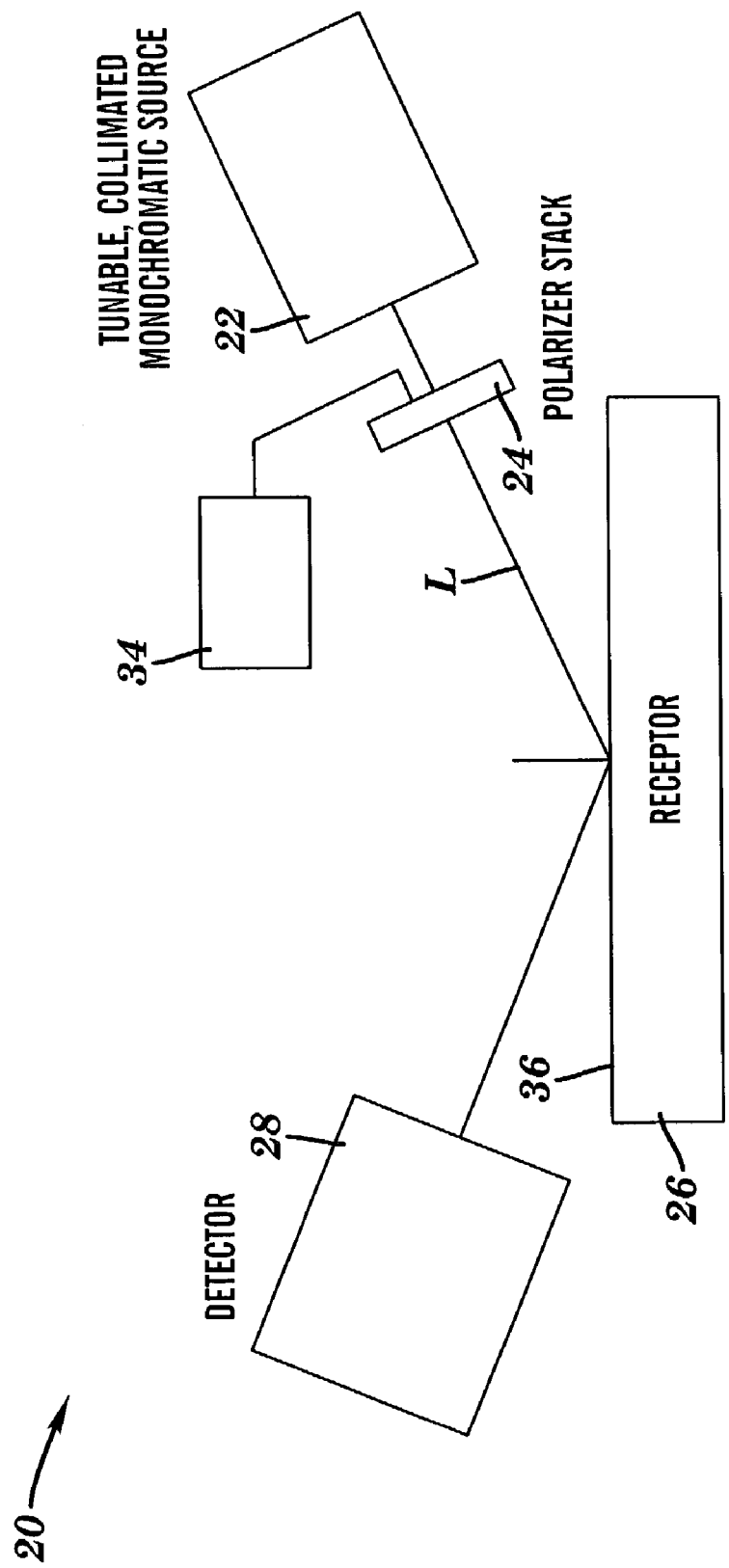
FIG. 1 is a block diagram of a biomolecular sensing system in accordance with one embodiment of the present invention.

A biomolecular sensing system 20 in accordance with one embodiment of the present invention is illustrated in FIG. 1. The sensing system 20 includes a light source 22, a polarizer 24, a receptor 26, and a detector 28, although the biomolecular system can have other types and arrangements of components. The present invention provides a system and method for detecting molecular adsorption based on simple reflectivity.

Referring more specifically to FIG. 1, the light source 22 in the sensing system 20 generates and transmits a light at a set wavelength towards a surface of the receptor 26. In this particular embodiment the light source 22 is a tunable, collimated, monochromatic light source, although other types of light sources, such as a light source which is monochromatic, but not tunable or collimated could be used. A variety of different types of light sources, such as a light-emitting diode, a laser, or a lamp with a narrow bandpass filter, can be used. The medium in which the light travels from the light source 22 and polarizer 24 to the receptor 26 is air, although other types of mediums, such as an aqueous environment could be used.

The polarizer 24 is positioned in the path of the light from the light source 22 and polarizes the light in a single direction, although other arrangements for polarization are possible. Any of a variety of polarizers can be used to satisfactorily eliminate the p-component of the light from the light source 22. The polarizer 24 may also be connected to a rotational driving system 34, such as a step motor, which can rotate the polarizer 24 in the path of the light from the light source 22, although other types of systems and arrangements for achieving this rotation can be used. Rotating the polarizer 24 (i.e. doing a full ellipsometric measurement) with the rotational driving system 34 results in even better sensitivity of the system.

As an alternative to using a polarizer in addition to a non-polarized light source, a polarized light source can be utilized. A number of lasers are known to emit polarized light.

Figure 2:
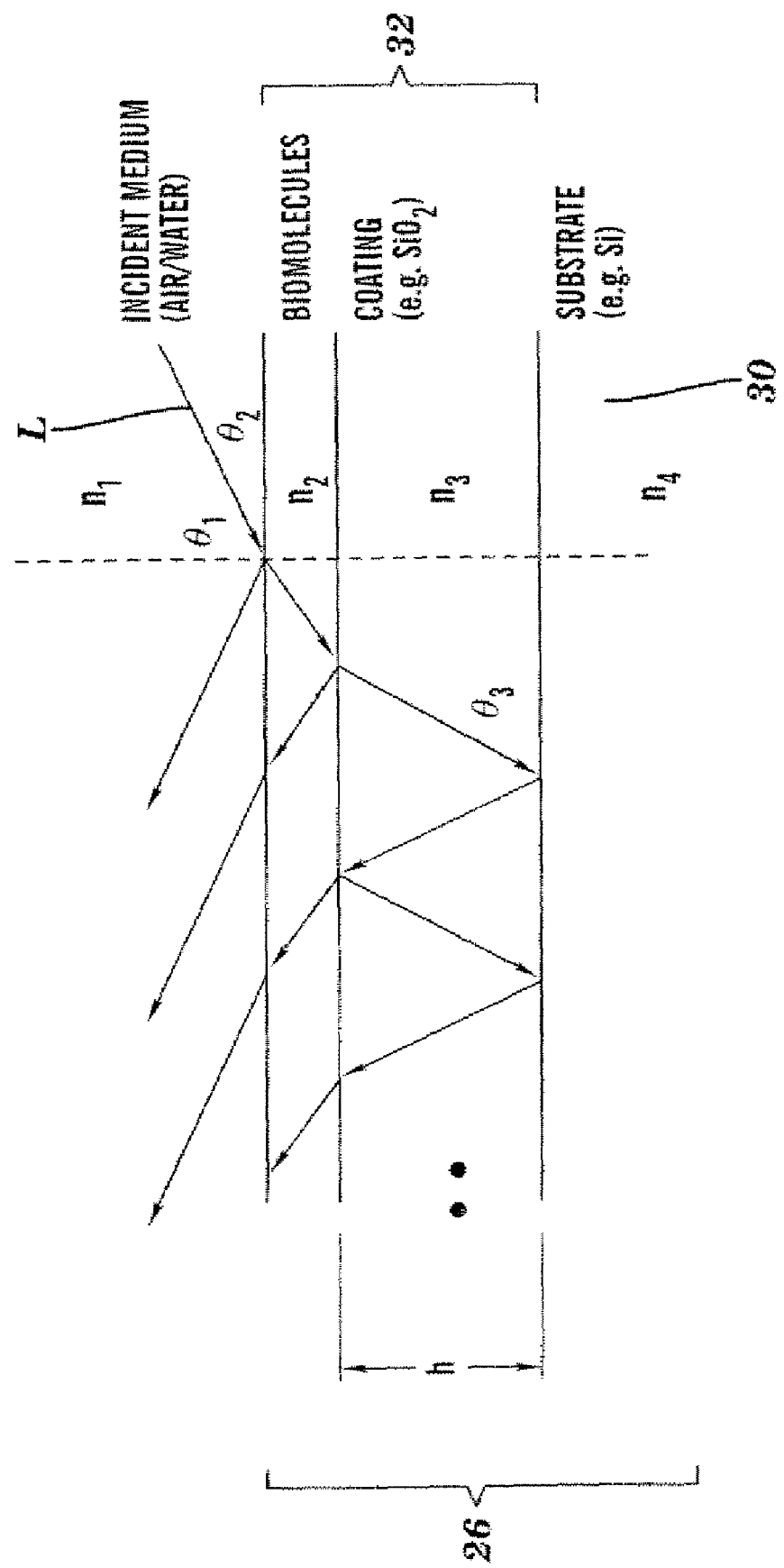
FIG. 2 is a side, cross sectional block diagram of a receptor for the biomolecular sensing system in accordance with one embodiment of the present invention.

The receptor 26 is positioned in the path of the polarized light from the polarizer 24 and includes a surface which is receptive to adsorption of one or more targets. In this particular embodiment, the receptor 26 has a substrate 30 made of silicon with a coating 32 made of silicon dioxide on one surface as shown in FIG. 2, although other types of receptors made of other materials and layers can be used. The coating 32 contains front and back surfaces, the front surface being presented to the media in which the receptor exists and the back surface being in contact with the substrate.

It should be appreciated by those of ordinary skill in the art that any of a variety of substrates can be employed in the present invention.

The coating on the substrate is a reflective coating, that is, both the front and back surfaces of the coating are capable of reflecting incident light as illustrated in FIG. 2. The front and back face reflections result in destructive interference that can be measured. As described in further detail hereinafter, the adsorbing target biomolecules effectively change the coating thickness to afford a change in the destructive interference pattern of reflected light.

A number of suitable coatings can be employed on the substrate. Silicon dioxide (glass) is a convenient coating because it can be grown very transparent and the binding chemistries are already worked out in many cases. Other transparent glasses and glass ceramics can also be employed. In addition, the coating can be a polymer layer or silicon nitride or an evaporated molecular layer. Coating procedures for application of such coatings onto substrates are well known in the art. It should also be appreciated that certain materials inherently contain a transparent oxidized coating thereon and, therefore, such receptor surfaces inherently include a suitable coating.

The coating itself may be capable of adsorbing a biomolecule under certain conditions. By altering the aqueous environment in which a target molecule resides, it is possible to precipitate target molecules onto the coating surfaces. Approaches for modifying the aqueous environment include, without limitation, altering pH, altering ionic strength of salt concentrations, or introducing modifiers such as non-surface bound antibodies capable of binding to and precipitating target molecules. Other known approaches can also be employed; however, such techniques are distinguishable from the use of blocking agents (e.g., bovine serum albumin or TWEEN-20) that inhibit nonspecific binding.

Alternatively, the coating of the receptor can be functionalized to include an adsorbate that is specific for a desired target molecule. In the embodiment illustrated in FIG. 2, the silicon dioxide coating on the surface of the receptor readily lends itself to modification to include thereon an adsorbate ($n_2$) that is receptive to adsorption of the one or more targets in the sample.

As used herein, the term adsorbate refers to a compound that is attached to the coating on the receptor via a coating-binding group and also includes one or more target-binding groups. Suitable adsorbates include, without limitation, non-polymeric small molecules, polypeptides or proteins, and oligonucleotides, although other biological and non-biological adsorbates can be utilized. The coating-binding group is typically a hydroxyl or epoxy group, particularly where an oxidized coating surface is provided on the receptor. The one or more target-binding groups can include, without limitation, an amino group, a thiol, a hydroxyl, an alkyl chain, an ester, a carboxylic acid, an aromatic, a heterocycle, or a combination thereof.

Exemplary non-polymeric small molecules include, without limitation: avidin, peptido-mimetic compounds, and vancomycin. One class of peptido-mimetic compounds is disclosed in U.S. patent application Ser. No. 09/568,403 to Miller et al., filed May 10, 2000, which is hereby incorporated herein by reference in its entirety. A preferred peptido-mimetic compound which binds to lipopolysaccharide is a tetratryptophan ter-cyclopentane ("TWTCP") as disclosed in the above-noted application to Miller et al. Another class of peptidomimetic compounds that binds to the *E. coli* membrane protein Intimin is disclosed in U.S. Provisional Patent Application Ser. No. 60/408,403, filed Sep. 5, 2002, which is hereby incorporated herein by reference in its entirety.

Exemplary polypeptides include, without limitation, a receptor for cell surface molecule or fragment thereof; a lipid A receptor; an antibody or fragment thereof; peptide monobodies of the type disclosed in U.S. patent application Ser. No. 09/096,749 to Koide, filed Jun. 12, 1998, and U.S. patent application Ser. No. 10/006,760 to Koide, filed Nov. 19, 2001, each of which is hereby incorporated by reference in its entirety; a lipopolysaccharide-binding polypeptide; a peptidoglycan-binding polypeptide; a carbohydrate-binding polypeptide; a phosphate-binding polypeptide; a nucleic acid-binding polypeptide; and polypeptides which bind organic warfare agents such as tabun, sarin, soman, GF, VX, mustard agents, botulinium toxin, *Staphylococcus* entertoxin B, and saitotoxin.

Exemplary oligonucleotide adsorbates can be DNA, RNA, or modified (e.g., propynylated) oligonucleotides of the type disclosed in Barnes et al., *J. Am. Chem. Soc.* 123:4107-4118 (2001), and Barnes et al., *J. Am. Chem. Soc.* 123:9186-9187 (2001), each of which is hereby incorporated by reference in its entirety. The oligonucleotide adsorbates can be any length which is suitable to provide specificity for the intended target. Typically, oligonucleotide adsorbates which do not contain modified nucleotides will be at least about 12 to about 100 nucleotides in length. For oligonucleotides which contain modified bases, oligonucleotides should be at least about 7 nucleotides in length, up to about 100 nucleotides in length.

Target molecules that can be bound by the adsorbate include, without limitation: proteins (including without limitation enzymes, antibodies or fragments thereof), glycoproteins, peptidoglycans, carbohydrates, lipoproteins, a lipoteichoic acid, lipid A, phosphates, nucleic acids which are possessed or expressed by certain pathogens (e.g., bacteria, viruses, multicellular fungi, yeasts, protozoans, multicellular parasites, etc.), whole cells or particles such as viral particles, or organic compounds such as naturally occurring toxins or organic warfare agents, etc. These target molecules can be detected from any source, including food samples, water samples, homogenized tissue from organisms, air, etc.

A number of strategies are available for attaching the one or more adsorbates to the coating surface of the receptor, depending upon the type of adsorbate which is ultimately to be attached thereto.

The available strategies for attaching the one or more adsorbates include, without limitation, covalently bonding an adsorbate to the coating, ionically associating the adsorbate with the coating, adsorbing the adsorbate onto the coating, or the like. Such association can also include covalently or noncovalently attaching the adsorbate to another moiety (of a coupling agent), which in turn is covalently or non-covalently attached to the coating of the receptor.

Basically, the oxidized and hydrolyzed surface of the coating is first functionalized (i.e., primed) with a coupling agent which is attached to the surface thereof. This is achieved by providing a coupling agent precursor and then covalently or non-covalently binding the coupling agent precursor to the coating surface. The primed surface is denoted 32' in FIGS. 13A-B and 14A-E. Once the coating surface has been primed, the adsorbate is exposed to the primed coating surface under conditions effective to (i) covalently or non-covalently bind to the coupling agent or (ii) displace the coupling agent such that the adsorbate covalently or non-covalently binds directly to the coating surface. The binding of the adsorbate to the receptor coating is carried out conditions which are effective to allow the one or more target-binding groups thereon to remain available for binding to the target molecule. The resulting functionalized coating is designated 32" in FIGS. 13A-B and 14A-E.

Suitable coupling agent precursors include, without limitation, silanes functionalized with an epoxide group, a thiol, or an alkenyl; and halide containing compounds.

Silanes include a first moiety which binds to the coating surface and a second moiety which binds to the adsorbate. Preferred silanes include, without limitation, 3-glycidoxypropyltrialkoxysilanes with C1-6 alkoxy groups, trialkoxy (oxiranylalkyl)silanes with C2-12 alkyl groups and C1-6 alkoxy groups, 2-(1,2-epoxycyclohexyl)ethyltrialkoxysilane with C1-6 alkoxy groups, 3-butenyl trialkoxysilanes with C1-6 alkoxy groups, alkenyltrialkoxysilanes with C2-12 alkenyl groups and C1-6 alkoxy groups, tris[(1-methylethenyl)oxy]3-oxiranylalkyl silanes with C2-12 alkyl groups, [5-(3,3-dimethyloxiranyl)-3-methyl-2-pentenyl]trialkoxysilane with C1-6 alkoxy groups, (2,3-oxiranediyldi-2,1-ethanediyl)bis-triethoxysilane, trialkoxy[2-(3-methyloxiranyl)alkyl]silane with C1-6 alkoxy groups and C2-12 alkyl groups, trimethoxy[2-[3-(17,17,17-trifluoroheptadecyl)oxiranyl]ethyl]silane, tributoxy[3-[3-(chloromethyl)oxiranyl] 2-methylpropyl]silane, and combinations thereof. Silanes can be coupled to the receptor coating according to a silanization reaction scheme shown in FIG. 13A, the conditions for which are well known to those of skill in the art. See also U.S. patent application Ser. No. 10/082,634 to Chan et al., filed Feb. 21, 2002, which is hereby incorporated herein by reference in its entirety.

Halides can also be coupled to the receptor coating according to the reaction scheme set in FIG. 13B, the conditions for which are well known to those of skill in the art.

Thereafter, the one or more adsorbates are bound to the receptor coating according to the type of functionality provided by the coupling agent. Typically, adsorbates are attached to the coupling agent or displace the coupling agent for attachment to the receptor coating in aqueous conditions or aqueous/alcohol conditions.

Epoxide functional groups can be opened to allow binding of amino groups according to the reaction scheme set forth in FIG. 14A, the conditions for which are well known to those of skill in the art. See also U.S. patent application Ser. No. 10/082,634 to Chan et al., filed Feb. 21, 2002, which is hereby incorporated herein by reference in its entirety. Epoxide functional groups can also be opened to allow binding of thiol groups or alcohols according to the reaction scheme set forth in FIGS. 14B-C, respectively, the conditions for which are well known to those of skill in the art.

Alkenyl functional groups can be reacted to allow binding of alkenyl groups according to the reaction scheme set forth in FIG. 14D, the conditions for which are well known to those of skill in the art.

Where a halide coupling agent is employed, the halide coupling agent is typically displaced upon exposing the primed receptor coating to one or more adsorbates which contain alcohol groups as the coating-binding groups. The displacement can be carried out according to the reaction scheme set forth in FIG. 14E, the conditions for which are well known to those of skill in the art.

Where the one or more adsorbates contain two or more target-binding groups, it is possible that the target-binding groups may also interact and bind to the primed surface of the receptor coating. To preclude this from occurring to any significant extent, the primed receptor coating can also be exposed to a blocking agent. The blocking agent essentially minimizes the number of sites where the one or more adsorbates can attach to the surface of the receptor coating. Exposure to the blocking agent can be carried out prior to exposing the primed receptor coating to the adsorbates or simultaneous therewith, although simultaneous exposure is generally preferred. The blocking agents can be structurally similar to the adsorbates except that they lack a target-binding group or the blocking agents can simply be simple end-capping agents. By way of example, an amino acid alkyl ester (e.g., glycine methyl ester, glycine ethyl ester, 3-alanine methyl ester, etc.) blocking agent can be introduced to an epoxide-functionalized receptor coating as shown in FIG. 13A for attaching an adsorbate to the coupling agent, except with the amino group of glycine opening the epoxide ring and covalently binding to the coupling agent.

Referring back to FIG. 1, the detector 28 is positioned to measure the reflected light from the receptor 26. In this particular embodiment, the detector 28 measures the amplitude of the reflected light at a single polarization and ignores phase, although the detector 28 could measure for other characteristics in the reflected light. As noted above, the interference between reflected light from the front and back coating surfaces is detected and a change in the interference pattern afforded by a particular coating results from adsorption of a target molecule to the coating surface (i.e., effectively increasing the thickness of the coating). A variety of different types of detectors can be used, such as a spectrometer.

Equations to model the system shown in FIGS. 1 and 2 are set below: The s-polarized reflectivity of the structure in FIG. 2 is R where $$R=|r|^2 \text{ and}$$

$$r=[(m_{11}+m_{12}p_n)p_1-(m_{21}+m_{22}p_n)]/[(m_{11}+m_{12}p_n)p_1+(m_{21}+m_{22}p_n)]$$

$p_1$ and $P_n$ apply to the first and last layer and are given by $p=(\epsilon/\mu)^{1/2}\cos\theta$ where $\epsilon$ and $\mu$ are the electric and magnetic permitivities and $\theta$ is the angle of propagation in the relevant layer.

$m_{ij}$ (with i and j being integers) are the elements of the overall transfer matrix $M(z_n)$, which is the product of the transfer matrices for each layer.

$$M(z_n)=M'_1(z_1)M'_2(z_2-z_1)\ldots M'_n(z_n-z_{n-1}) \text{ where:}$$

$$m'_{11}=m'_{22}=\cos(k_0 nz\cos\theta)$$

$$m'_{12}=-(i/p)\sin(k_0 nz\cos\theta) \text{ and}$$

$$m'_{21}=-ip\sin(k_0 nz\cos\theta)$$

are the matrix elements of M'.

$k_0=2\pi/\lambda$ where $\lambda$ is the free space wavelength of the probe light. The square root of −1 is denoted by i, n is the index of refraction and z is the spatial coordinate normal to the coating.

In FIG. 2 the propagation angles for the light are denoted by $\theta$ and refractive indices by n. The coating 32 has a thickness h and the incident medium and the substrate 30 of the receptor 26 are assumed to be semi-infinite. It is assumed that there is a binder layer (not shown) between the coating 32 and the target analyte. It is also assumed that the binder layer has the same refractive index as the coating 32 and merely represents an increase in the thickness h of the coating 32.

Referring to FIGS. 1 and 2, the light source 22 is positioned to direct the light at the coating 32 on the substrate 30 at an angle of incidence which results in near perfect interference. When you are near this condition where there is no reflectivity, small changes in the absorption of a target or targets in the receptor 26 will cause large changes in reflectivity which can be easily measured. By way of example only, an angle of incidence $\theta_1\theta_4$ in air that is close to 70.5 degrees is optimal for red probe colors. The physical reason that substantially larger angles do not work well is that the reflection from the surface of the target becomes too large at glancing incidence to be cancelled by the reflection from the surface of the coating 32. For s-polarization and angles substantially smaller than 70.5 degrees, the back reflection from the highly reflective substrate 30 is too large to be cancelled by the front face reflection. Incomplete cancellation at incidence angles other than 70.5 degrees still leads to small effects, but optimization of the angle of incidence makes the system extremely sensitive. Where sensitivity requirements are not as stringent, a wider range for the angle of incidence can be employed for a particular substrate/coating embodiment.

The modeling above assumes that the measurement takes place on a surface that has been dried. In many cases, this is impractical or undesirable. For example, prior to measuring a dry surface 36 on the receptor 26, it may be necessary to rinse the surface 36. Unfortunately, rinsing of the surface 36 may unbind the analyte from the substrate 30, as in the case of dehybridization of DNA in the absence of salt.

Figure 3:
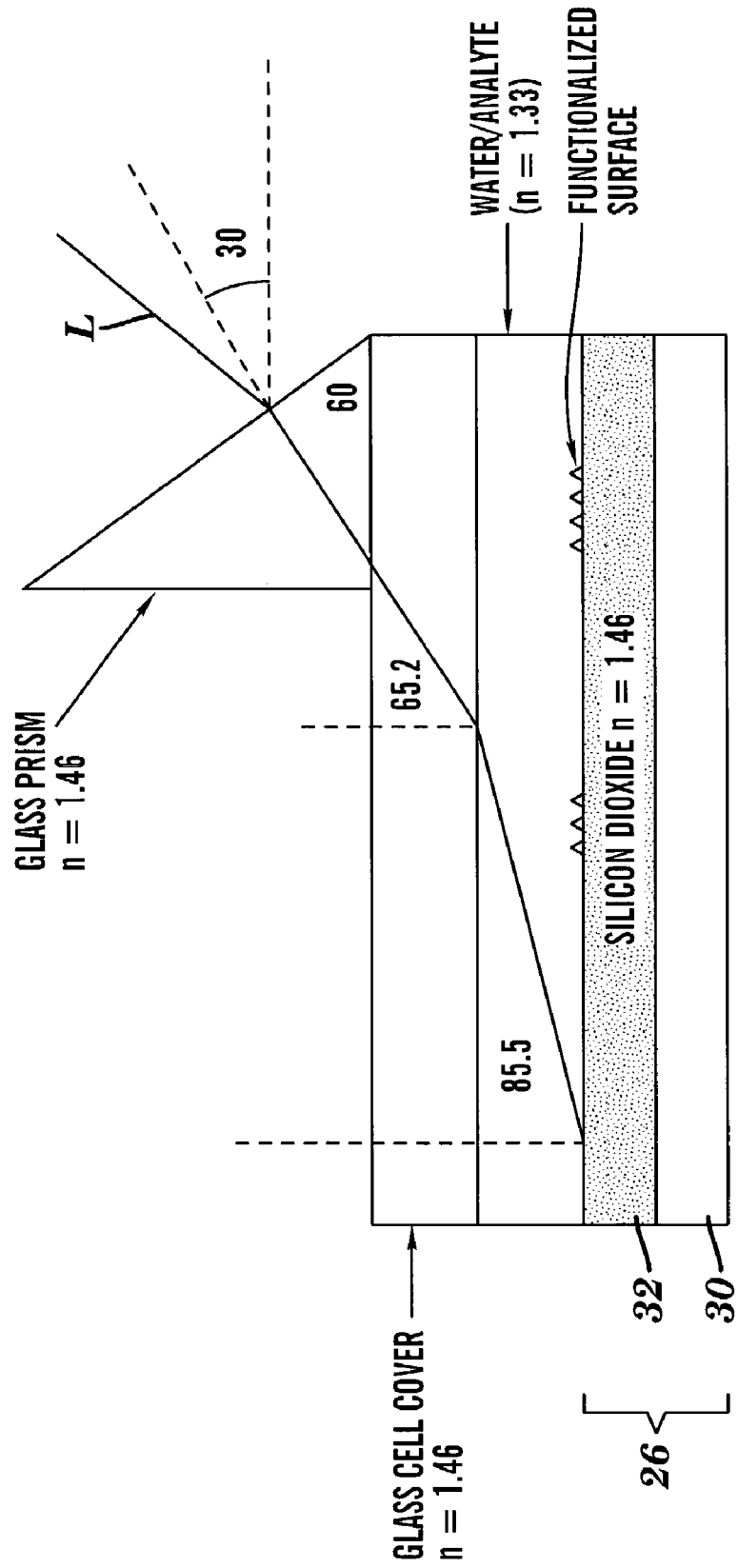
FIG. 3 is a side, cross sectional block diagram of a receptor for the biomolecular sensing system in accordance with another embodiment of the present invention.

One of the advantages of the present invention is that it also works in an aqueous environment as shown in FIG. 3. In this particular embodiment, when the medium of incidence is water (refractive index=1.33), then the optimal ratio of oxide thickness to wavelength is approximately 0.409 at red wavelengths and the optimal angle of incidence $\theta_1\theta_4$ is about 85.5 degrees. In order to achieve this, coupling from the air with a prism is necessary. A sixty degree prism with the light incident about seven degrees off the long face normal will work to get the optimal angle of incidence in this particular embodiment. The line L in FIG. 3 represents the path of the light and the exit would be through a symmetrically placed outcoupling prism (not shown). Use of higher index interlayers for the receptor 26 can reduce this optimal angle of incidence $\theta_1\theta_4$ of about 85.5 degrees. For example, a receptor 26 with a silicon wafer coated with silicon nitride or titanium dioxide followed by silicon dioxide, can be engineered to use the same chemistry (appropriate to the silicon dioxide), but with a smaller angle of incidence.

Working in aqueous environment has many advantages, such as being able to use bodily fluids directly, eliminating the need for a rinsing step, and being able to monitor the binding kinetics. The ability to monitor the kinetics is useful in differentiating perfect oligonucleotide sequence matches from analytes with single base pair mismatches. Using fluorescent detection in an aqueous measurement is problematic since the entire liquid above the functionalized substrate 30 will contain fluorescent analytes. Since the present invention is only sensitive to changes at the interface, working under liquid will not pose analogous difficulties.

Figure 4:
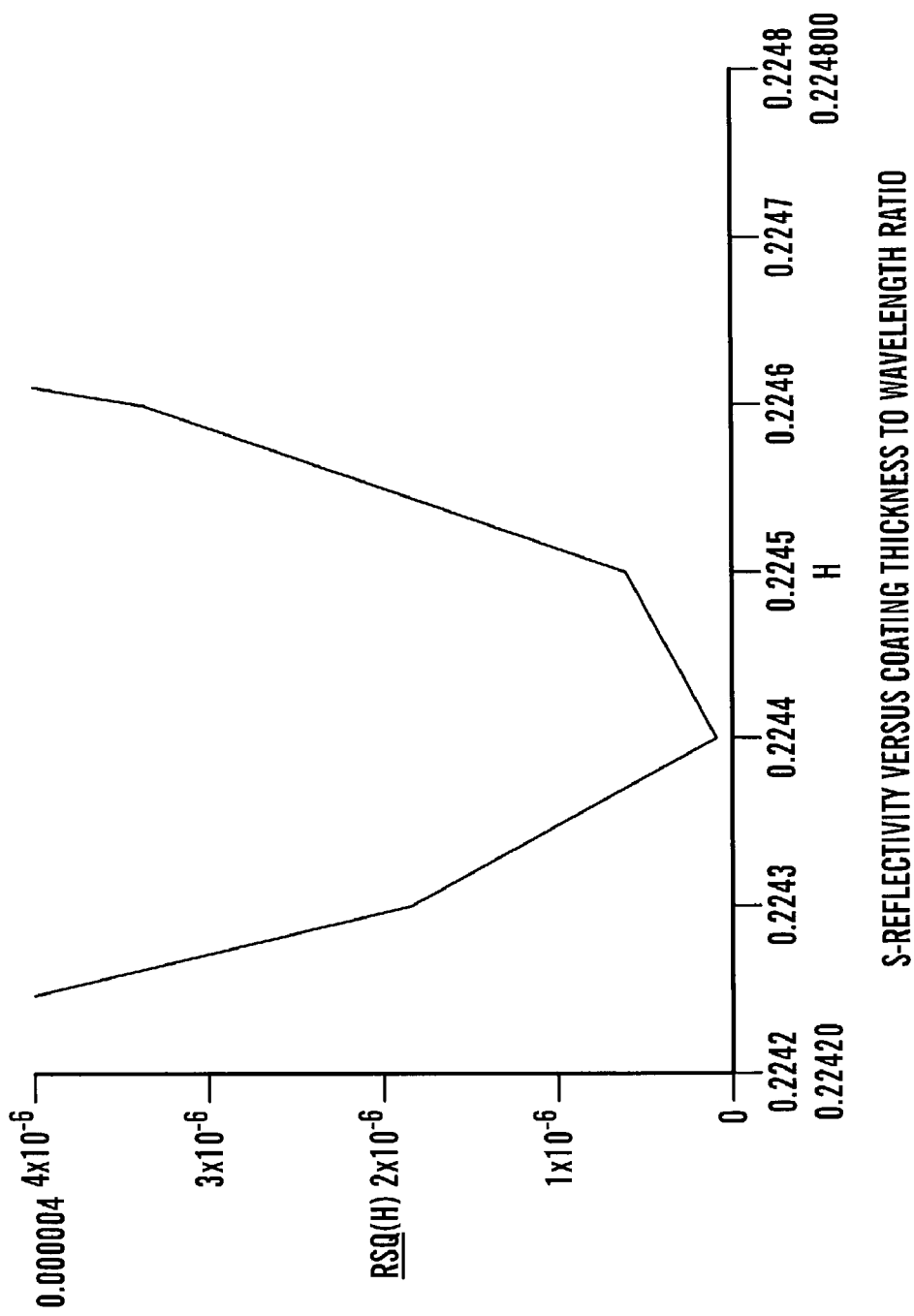
FIG. 4 is a graph of reflectivity versus coating thickness to wavelength ratio.

Referring back to FIGS. 1 and 2, given an incidence angle, there is an optimal ratio of the thickness h of the coating 32 to the wavelength $\lambda$ of the light. As can be seen in the modeling equations described earlier, only the ratio $H=h/\lambda$ is important so that the thickness of the coating 32 and the wavelength of the light enter symmetrically into the formalism. The ratio is approximately 0.2244 for the 70.5 degree incidence angle. This means, for example, that for a 148.7 nm thick structure the s-reflectivity minimum is at 662.65 nm. The result of a numerical computation for a receptor 26 with silicon oxide on silicon with no biomolecular layer is shown in FIG. 4. The addition of a target, such as biomolecules, to the coating 32 dramatically changes the position of the reflectivity minimum and the reflectivity at a given wavelength near the minimum.

This modeling also illustrates that, for this particular system, choice of longer wavelengths (>600 nm) is superior. The reason for this has to do with dispersion of the refractive index of silicon. As noted above, perfect cancellation is more difficult with absorbing substrates like silicon. Silicon becomes more absorbing as one goes nearer to its direct optical gap in the blue and the reduction of interference by adsorbates is a smaller effect.

A simple measurement scheme for the detector 28 is to monitor s-reflectivity from the coating 32 versus probe wavelength. The fact that the ratio h/$\lambda$ where near perfect cancellation of the reflectivity occurs is 0.2244 means that a 0.1 nm (1 Angstrom) change in thickness leads to about (0.1/0.2244≅0.5) nm change in the wavelength of minimum reflectivity. (Note: This assumes the refractive index of the analyte is about the same as that of the coating 32 of $SiO_2$. The index of Si near 650 nm is used for the entire calculation of FIG. 4. Relaxing these approximations makes little difference to the results). The position of the minimum is easily detectable to 0.5 nm using a lamp for the light source 22 and a spectrometer for the detector 28 so that one Angstrom resolution for the coating 32 plus adsorbate thickness can be easily achieved.

Figure 5:
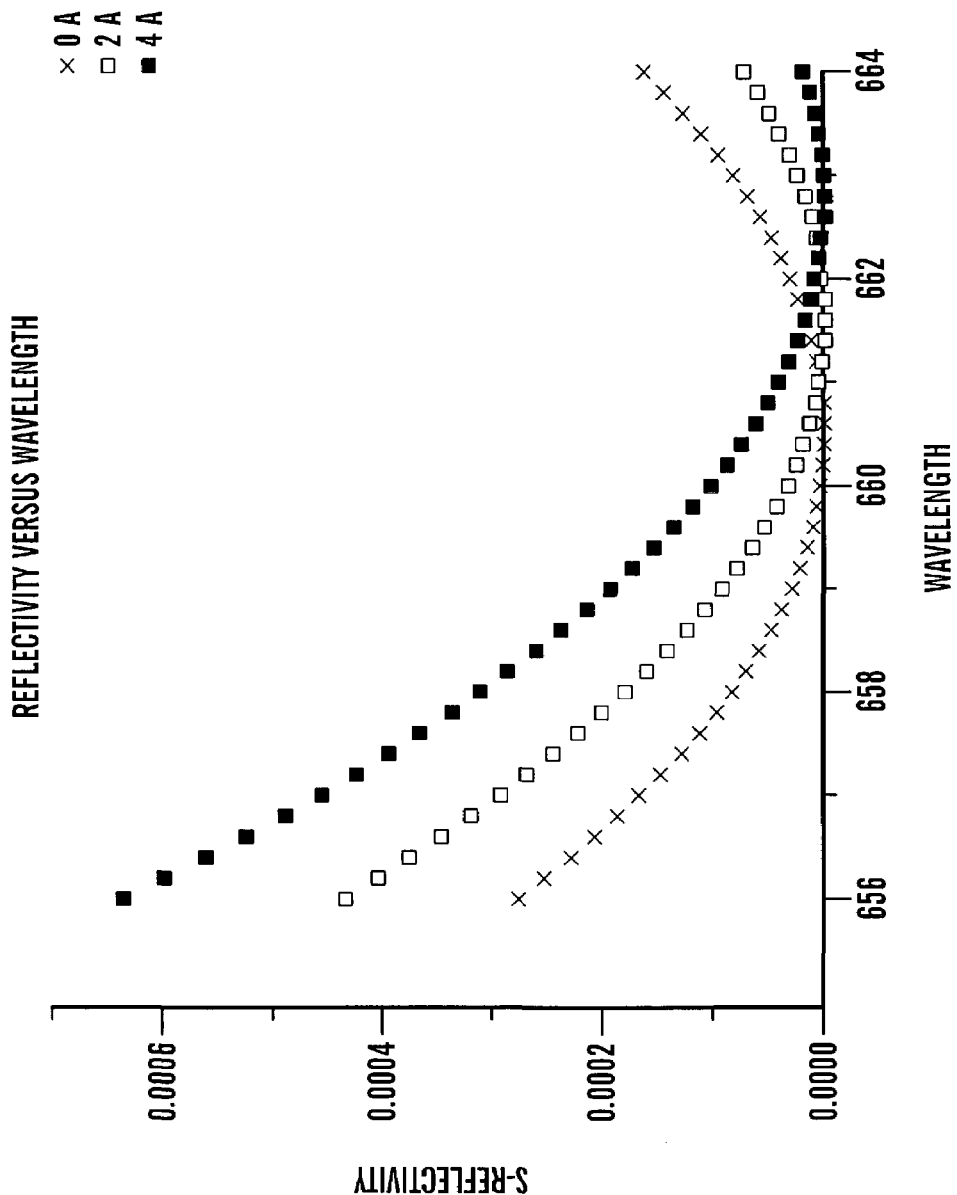
FIG. 5 is a graph of reflectivity versus wavelength with three different thicknesses of a biomolecule on the substrate in the receptor.

Referring to FIG. 5, a graph of the s-reflectivity versus wavelength for a coating 32 which is a 148.7 nm thick oxide with three different thicknesses of a biomolecule with n=1.55 adsorbed to the oxide is illustrated. The minima are extremely well defined and the reflectivity changes of factors of two are predicted for tiny sub-Angstrom changes in thickness. Thus, with higher spectral resolution, an extremely sensitive measurement with perhaps hundredth of a monolayer sensitivity or even less for larger adsorbates, like proteins or cells, is possible. Note that the case which has been modeled has a realistic surface roughness, finite bandwidth of the light, and finite angular divergence and the effects of molecular binding at the surface on reflectivity remain quite large.

A summary of the effects of these nonidealities is discussed with reference to FIGS. 8-10 below. The model used to determine the effect of binding at surfaces assumes that there is no surface roughness of the coating 32 (e.g. SiO2), that the reflected light is perfectly monochromatized and that the incident light is perfectly collimated. This example uses a receptor 26 with a Si/SiO2 structure adjacent an air medium with a 148.7 nm thick oxide and incorporates the effects of roughness in the oxide, finite bandwidth of light and angular divergence of the beam into the theory. Each of these nonidealities is discussed separately while the other two are assumed perfect for simplicity. However, modeling all three nonidealities together does not substantively alter the conclusions.

Figure 8:
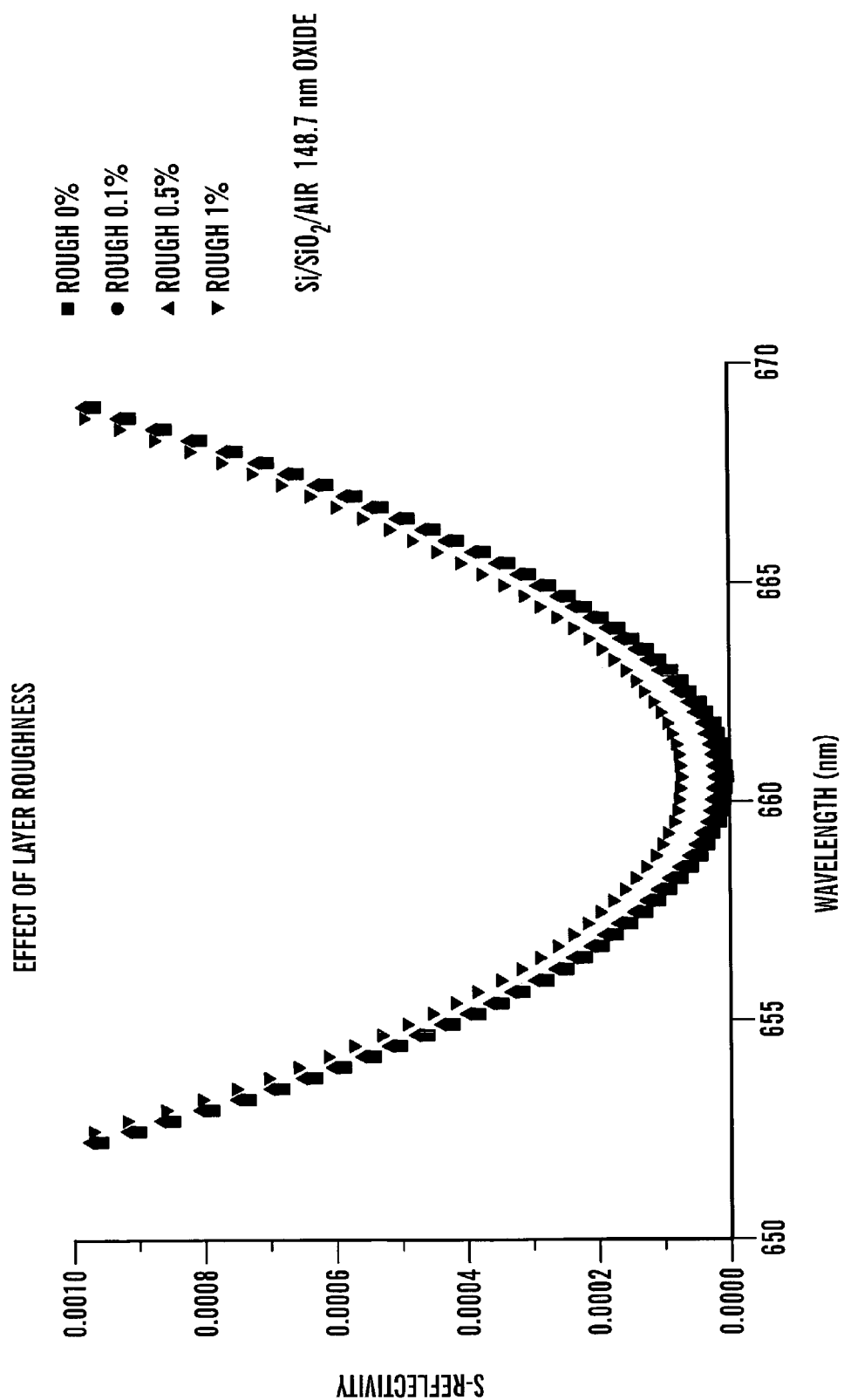
FIG. 8 is a graph of reflectivity versus wavelength for a surface with a rough oxide coating.

Referring to FIG. 8, a graph of reflectivity versus wavelength for a surface with a rough oxide coating 32 of average thickness 148.7 nm is illustrated. The figures listed in the legend in this graph are the percent roughness. By way of example, a 1% roughness means that the oxide varies 1.487 nm in thickness. This is easily obtained commercially and as shown has little material effect on the reflectivity curves on this scale.

Figure 9:
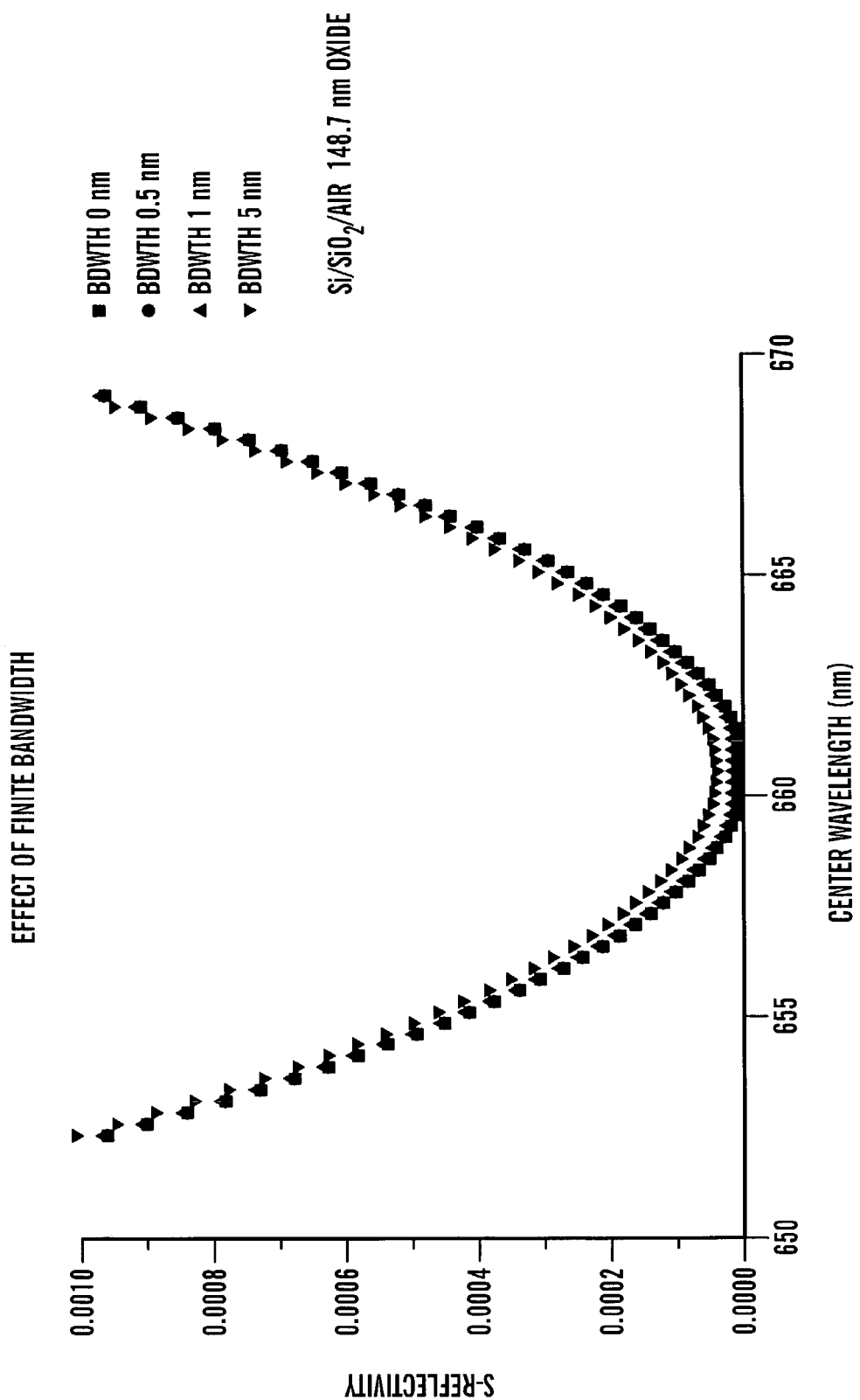
FIG. 9 is a graph of reflectivity versus wavelength for various bandwidth sources.

Referring to FIG. 9 a graph of reflectivity versus center wavelength for various bandwidth sources is illustrated. The figures listed in the legend in this graph are the assumed bandwidth in nm. Bandwidths of 0.5 nm are easily obtained with a spectrometer and perhaps a one nm with an interference filter. As shown, this has little material effect on the reflectivity curves on this scale.

Figure 10:
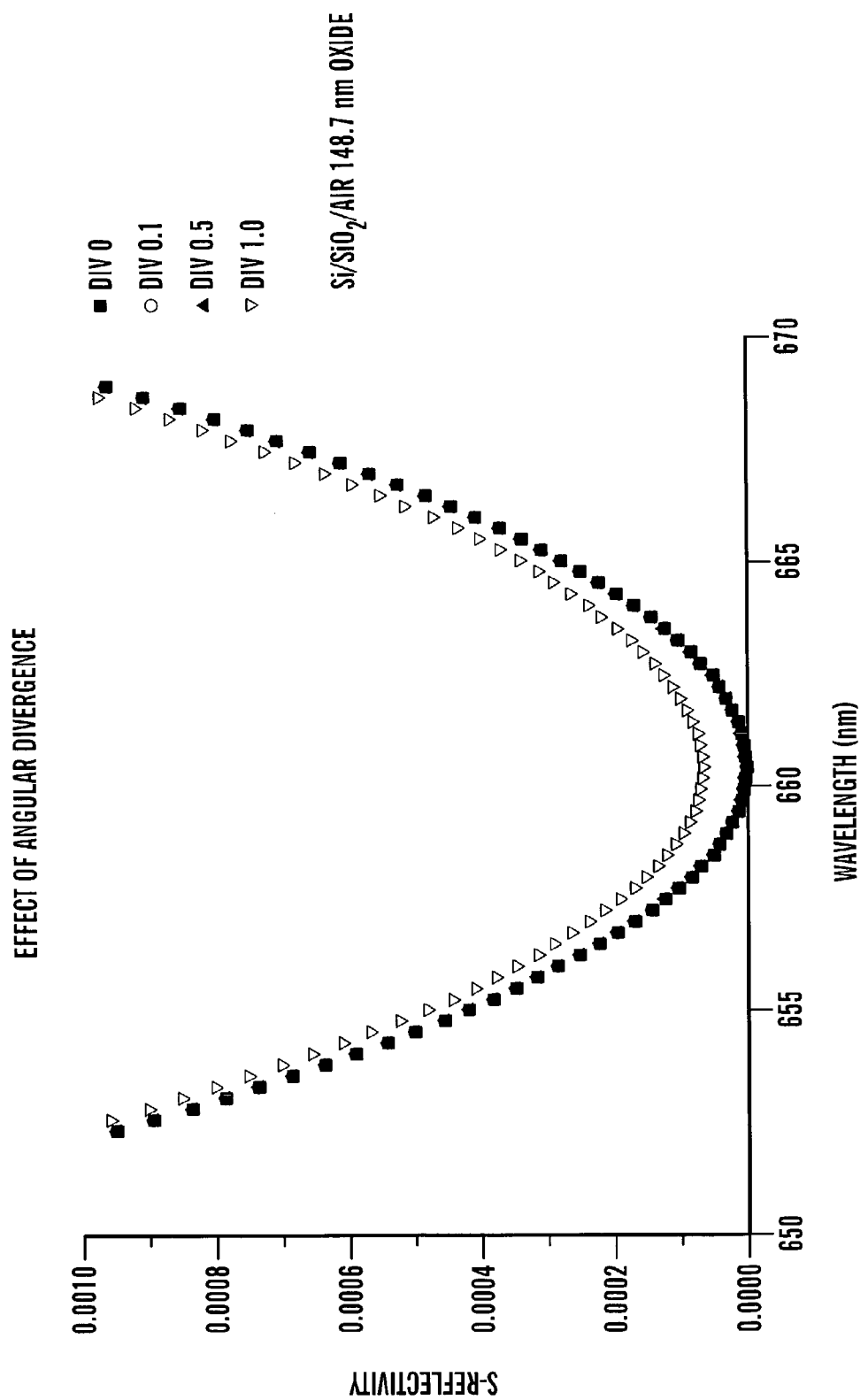
FIG. 10 is a graph of reflectivity versus wavelength with various angular divergences for the probe source.

Referring to FIG. 10, a graph of reflectivity versus wavelength with various angular divergences for the light source 22 is illustrated. In the legend, squares are perfect collimation, circles 0.1 degree divergence, up triangles are 0.5 degree divergence and down triangles are one degree divergence. There is almost no effect on the reflectivity on this scale until angular divergences of one degree. It should not be difficult to achieve collimation as good as 0.1 degrees (2 mrad). Note that if the region were expanded below 0.0001 large effects close to 660 nm would be observed on the minimum reflectivity. The upshot is that, if a simple method of mapping reflected intensity versus wavelength is used to determine the average thickness at a particular point, angular divergence would likely be limited so this is a very important parameter.

The calculations shown in FIGS. 8-10 demonstrate that sub-Angstrom resolution should be achievable for practically realizable conditions. For 100 micron spot sizes, this means that adsorption of 20-mers of untagged oligonucleotides should be detectable at the 0.1 femtomole level. As long as the roughness is on lateral length scales short compared to a wavelength, the probe light sees nearly the average thickness.

Figure 6:
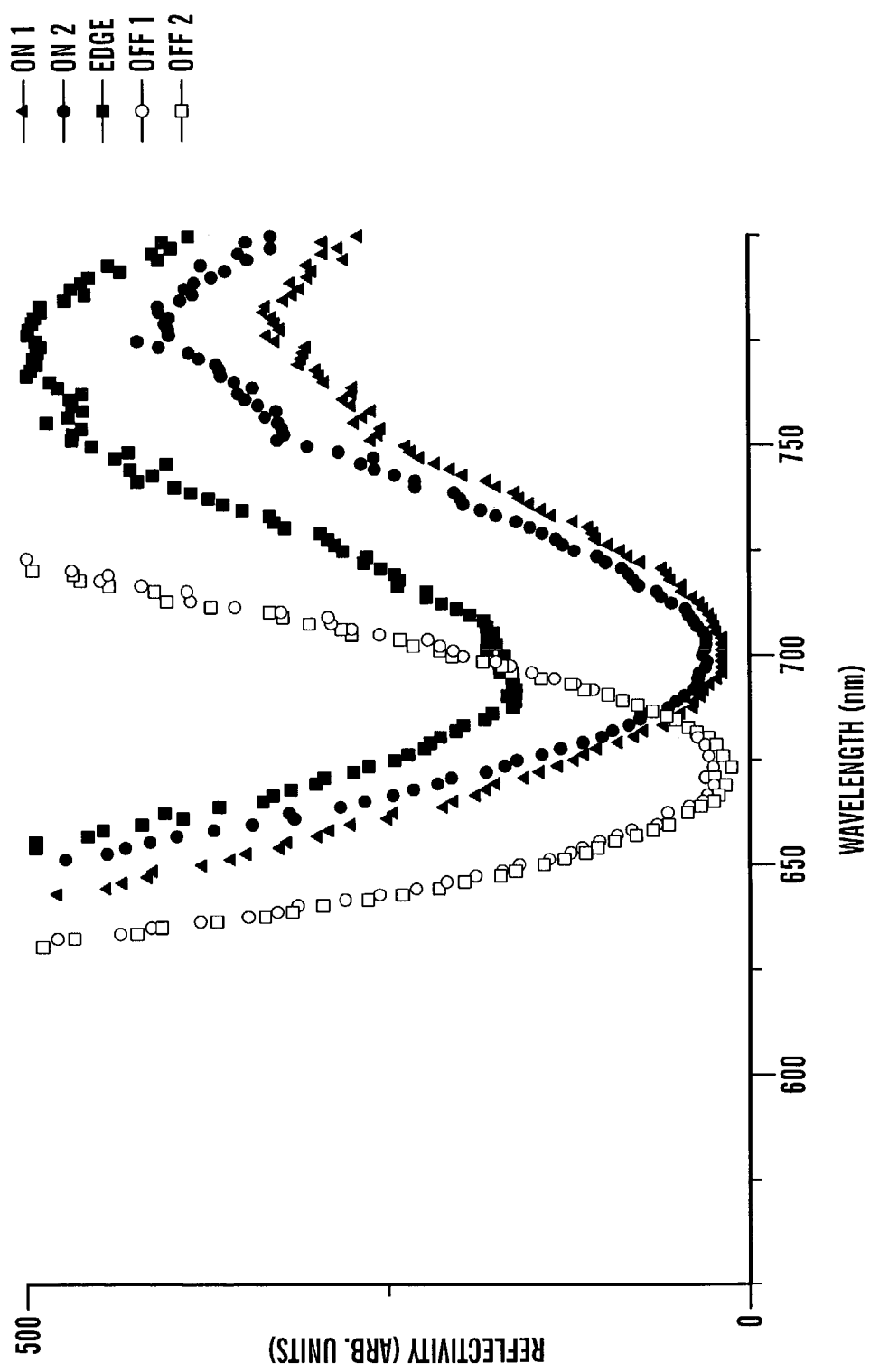
FIG. 6 is a graph of reflectivity versus wavelength for light striking different positions of the receptor.

Referring to FIG. 6, a graph of reflectivity versus wavelength for different positions on the coating 32 in the receptor 26, such as the one shown in FIGS. 1 and 2, that is epoxidated, spotted with TWTCP, and rinsed is illustrated. The amine groups of the TWTCP are known to bind to the epoxide and the thickness is therefore increased. In the graph, on1 and on2 are two different locations for the light on the spot while off1 and off2 are on the epoxidated, but not functionalized receptor 26. Edge is a point where part of the light is on the spot and part off. These data are recorded with a white light source for the light source 22 and a CCD spectrometer for the detector 28.

Figure 7:
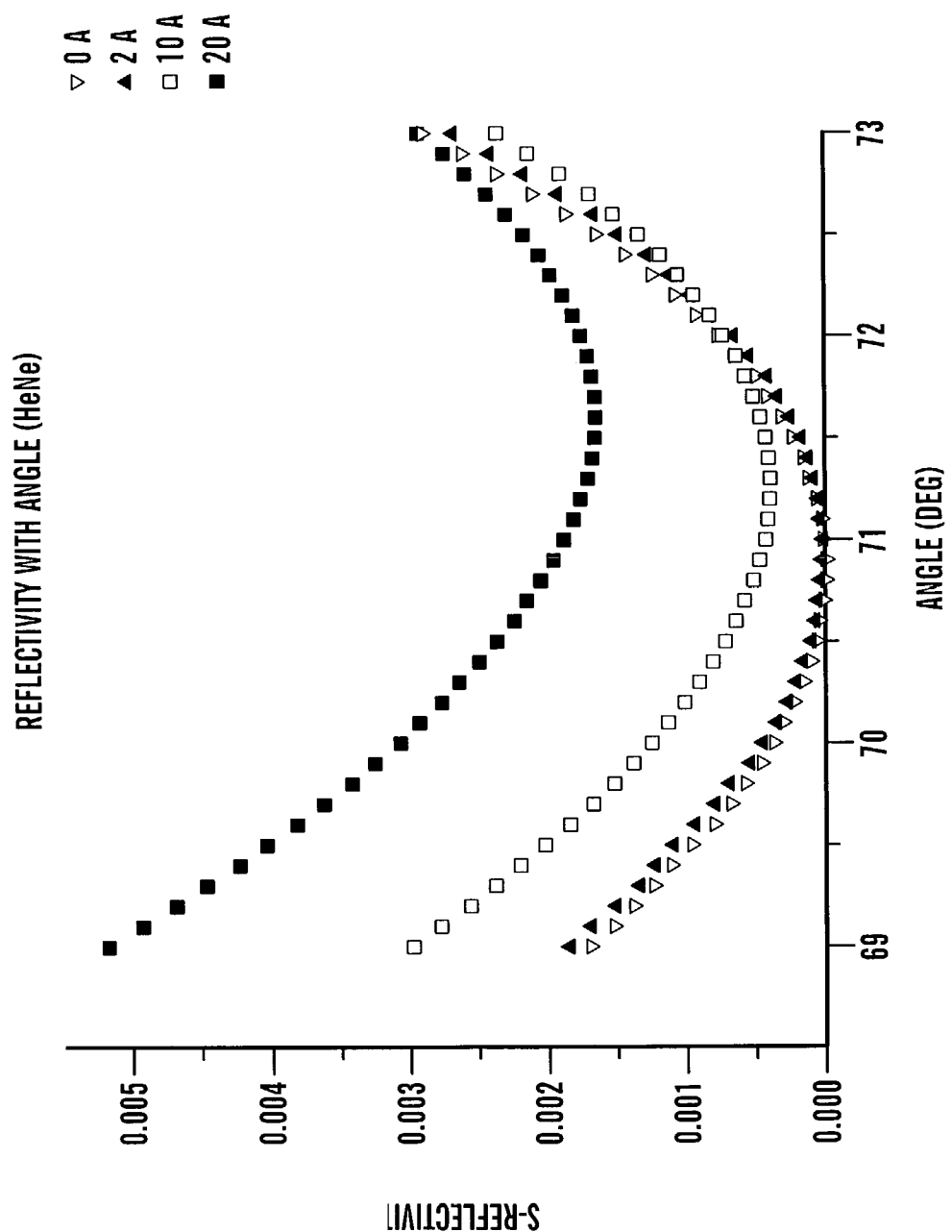
FIG. 7 is a graph of reflectivity versus angle for several different thicknesses of the absorbed layer.

Referring to FIG. 7, a graph of s-reflectivity variation with angle at 633 nm (HeNe laser wavelength) for several different thicknesses of adsorbed layer is shown. In this particular embodiment, the sensing system 20 has a monochromatic light source 22, such as a light emitting diode, laser, or lamp with a bandpass filter, and angle of incidence of the light is varied. As shown in the graph, the contrast between different thickness leads a very small change in minimal angle, so this system will be less sensitive, but this embodiment may be practical in some applications and alleviates the need for a light source 22 which is tunable. As shown in FIG. 7, the variation of intensity at the minimum varies significantly with overlayer thickness and could be used to develop a sensing scheme.

The simplest scheme of all for the sensing system 20 is to use a monochromatic source for the light source 22 and monitor reflectivity versus position or time with the detector 28. Optimization of this approach would require the tightest control on fabricating the receptor 26 since it would be important that the functionalized receptor 26 needs to have reflectivity minimum quite near the fixed wavelength to be employed. In one implementation of the fixed angle and wavelength sensor, reflectivity of a functionalized spot could be compared to a reference spot that would not bind the target biomolecule. Changes in the relative amounts of reflectivity upon exposure to the analyte would indicate binding. In another possible implementation, one could measure changes in s-reflectivity of a single functionalized spot using the p-polarized reflection as a normalization to correct for changes in source intensity.

The simple scheme for the sensor discussed above can also be used for larger scale arraying. The only difference is that the detector 28, such as a CCD camera, images a substantial portion of the coating 32 of the receptor 26. The advantages of arraying are obvious. One can do many simultaneous experiments, look for many different analytes or do pattern analysis where binding is not perfectly specific. Another advantage is that untreated areas can be easily used as a reference to more accurately measure the additional thickness due to analyte binding. Often, adsorption occurs nonuniformly (perhaps due to solvent evaporation during dosing causing droplets to shrink) so that the actually deposition of binder and analyte can be quite inhomogeneous. This can be detected more easily with an imaging method and one could apply numerical procedures similar to those used for fluorescent assays to properly account for the nonuniformity. The lateral spatial resolution will probably be determined by the amount of light in a given region of the detector 28 and may be as good as 10 microns (a typical CCD camera pixel dimension), easily compatible with state-of-the-art biological microarray printers.

The modeling of FIG. 5 makes it clear that, under conditions of perfect collimation, the sensitivity of the method to surface topology is limited by spectral resolution. When using a lamp for the light source 22 and a spectrometer for the detector 28, it is impractical to achieve better than perhaps a few Angstrom resolution and the cost of achieving it is loss of light intensity so that a much more sensitive detector 28 is required. One solution to this problem is to use Fourier transform methods that are often employed for high resolution visible spectroscopy. In this way, sub-Angstrom spectral resolution (which, as noted above, translates to hundredth Angstrom thickness resolution) should be achievable. Essentially, the light source 22 in FIG. 1 is replaced by the output of an interferometer from a traditional FTIR. The detector 28 can be replaced by a photodiode for single spot measurements or by a camera for simultaneous multiple spot measurements. In the latter case, it will be necessary to use step scan FTIR and separately Fourier transform each spot from many frames to recover their reflectivity spectra. The Fourier transform approach should improve spectral resolution and throughput.

Note that a tunable diode laser or dye laser can be used as the light source 22 to solve throughput and spectral resolution problems as well. These might be somewhat more difficult to implement in practice. A compromise solution might be to use a lamp and narrowband interference filter as the light source 22. Tuning would be achieved by tilting the filter off normal to move its pass band to the blue. A tilt of angle $\phi$, for example, would lead to moving the passband from normal incidence value $\lambda_0$ to $\lambda_0 \cos \phi$.

The structure in FIGS. 1 and 2 is only one example of using the angle enhanced interference effect, and the implementation using silicon with its thermal oxide is just one implementation found to be practical. It is clear that dielectric wavestacks with multiple layers or a simple layer of silicon nitride plus oxide on glass or titanium oxide plus oxide on glass will also work and be practical. Similarly, uniform polymer layers such as nitrocellulose used for biological assays or porous glasses may be viable coatings. Note however that silicon is easy to obtain and process and there is no reflection from the back side of the substrate 30.

Incorporating the modeling and the different possible arrangements discussed above, the operation of the sensing system 20 will be discussed with reference to FIGS. 1 and 2. Initially, a measurement may be taken before a sample which may contain one or more targets is introduced to the receptor 26. The light source 22 generates a monochromatic and collimated light at a set wavelength which is transmitted towards a coating 32 on the substrate 30 in the receptor 26, although other types of light can be generated and transmitted. The set wavelength is selected based on the angle of incidence and the thickness of and type of coating 32 on the substrate 30. The angle of incidence of the light with respect to the surface 36 of the receptor 26 is selected that results in near perfect interference The light is directed through a polarizer 24 which polarizes the light in a single direction, although other arrangements can be used. The polarized light strikes and is reflected off of the coating 32. As discussed earlier with reference to FIGS. 8-10, nonidealities, such as surface roughness, finite beam divergence, and finite bandwidth do not substantively alter the measurement results or sensitivity of the sensing system 20. The detector 28 measures the initial reflected light and produces an output of the initial measurement. The detector 28 may take an imaging array of the surface 36, like the one shown in FIG. 11.

Next, a sample with one or more targets (of the type described above) is introduced, near the receptor 26, thereby allowing the targets to attach to and/or be absorbed by the coating 32 in the receptor 26. Another measurement is taken after the sample is introduced to the receptor 26. The light source 22 again generates a monochromatic and collimated light at the set wavelength which again is transmitted towards the coating 32 on the substrate 30 in the receptor 26, although other types of light can be generated and transmitted. The light is again directed through the polarizer 24 which polarizes the light in a single direction, although other arrangements can be used. The polarized light strikes and is reflected off of the coating 32 absorbed targets. Absorbing the targets at the surface of the coating 32 dramatically disturbs the interference condition and leads to increased reflectivity. The detector 28 measures the exposed reflected light and produces another output of the exposed measurement. A variety of different processing techniques can be used on the initial and exposed measurement as required by the particular application, such as monitoring the growth of a particular target or identifying the presence of a particular target.

EXAMPLE

As an example, data from an experiment to detect oligonucleotides using the imaging version of the technique presented with reference to FIG. 5. However, any selective binding chemistry that can be implemented on the receptor 26 should produce an adequate sensor. In this example, the receptor 26 is rinsed and dried before imaging the surface topology of the coating 32. This is important to do to reduce any non-selective binding.

In this example, the surface is functionalized by silanization with 3-aminopropyltrimethoxysilane ("APTES") followed by glutaraldehyde ("GA") This in turn binds to streptavidin. This initial surface is relatively easy and rapid to prepare. The streptavidin surface is reasonably immune to non-specific binding and strongly binds biotinylated compounds. Since many biotinylated oligomers and antibodies are commercially available, this chemistry is easily implemented to make the receptor 26.

Figure 11:
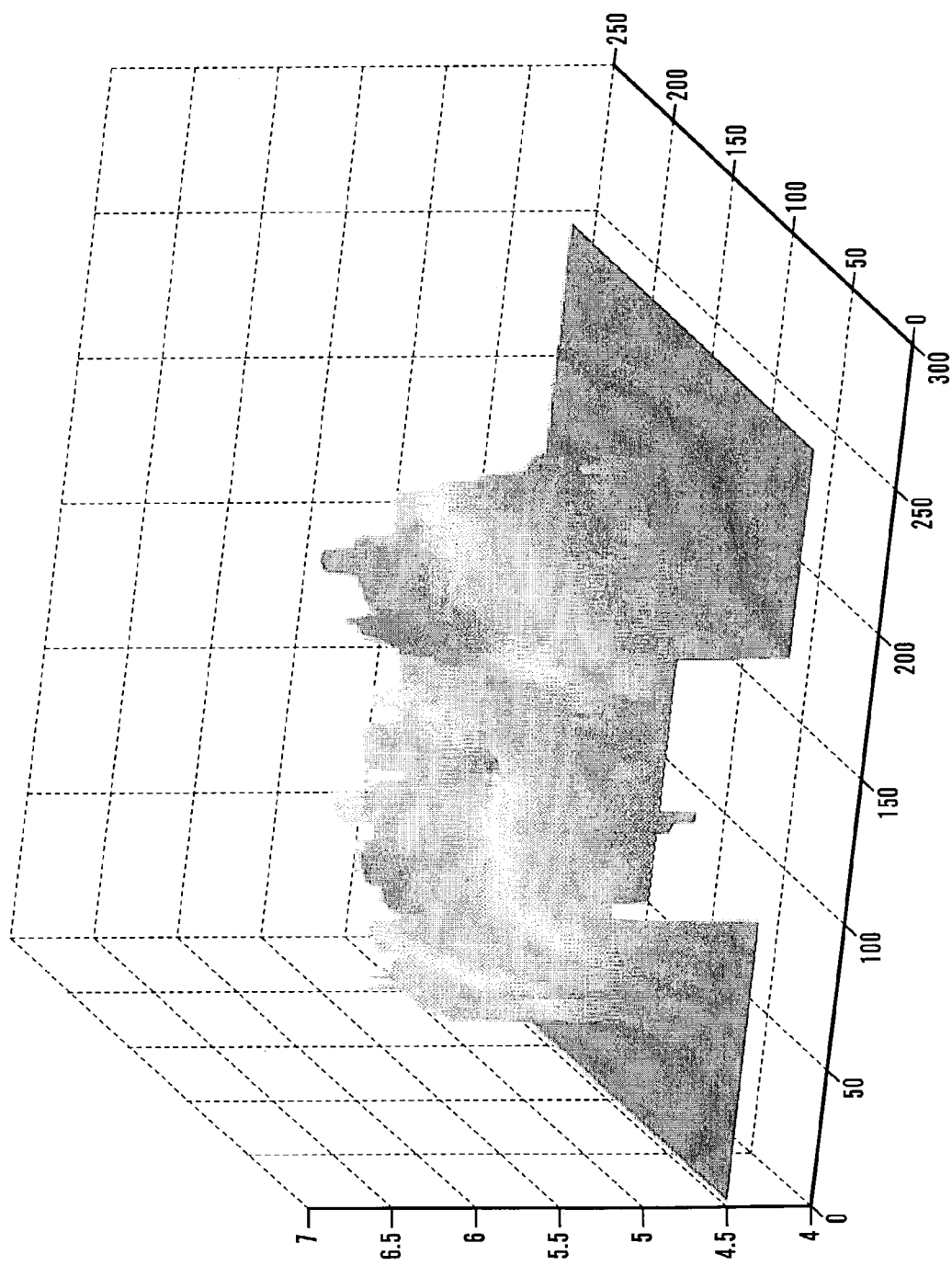
FIG. 11 is a three dimensional graph of spots of biotinylated DNA attached to a strepavidin functionalized surface.

Referring to FIG. 11, the surface topology of the receptor 26 is illustrated. The receptor 26 is undoped Si with a 151 nm thermal oxide. The vertical axis is in nm while the horizontal axes are labeled by pixel. The coating 32 on the receptor 26 is a streptavidin and the coating 32 has been hand spotted with two spots of biotinylated oligonucleotide with different sequences. The overall spot is approximately 1 cm in diameter. In this case, the light source 22 was a monochromatized lamp that could be varied in wavelength and the detector 28 was a CCD camera with 10 micron lateral resolution. The spots are approximately 2-3 mm in diameter. The vertical scale represents the spot height in nm and can therefore be used to calibrate the amount of bound material. The result for thickness agrees with those from spectroscopic ellipsometry in test cases with large areas where ellipsometry is practical.

Figure 12:
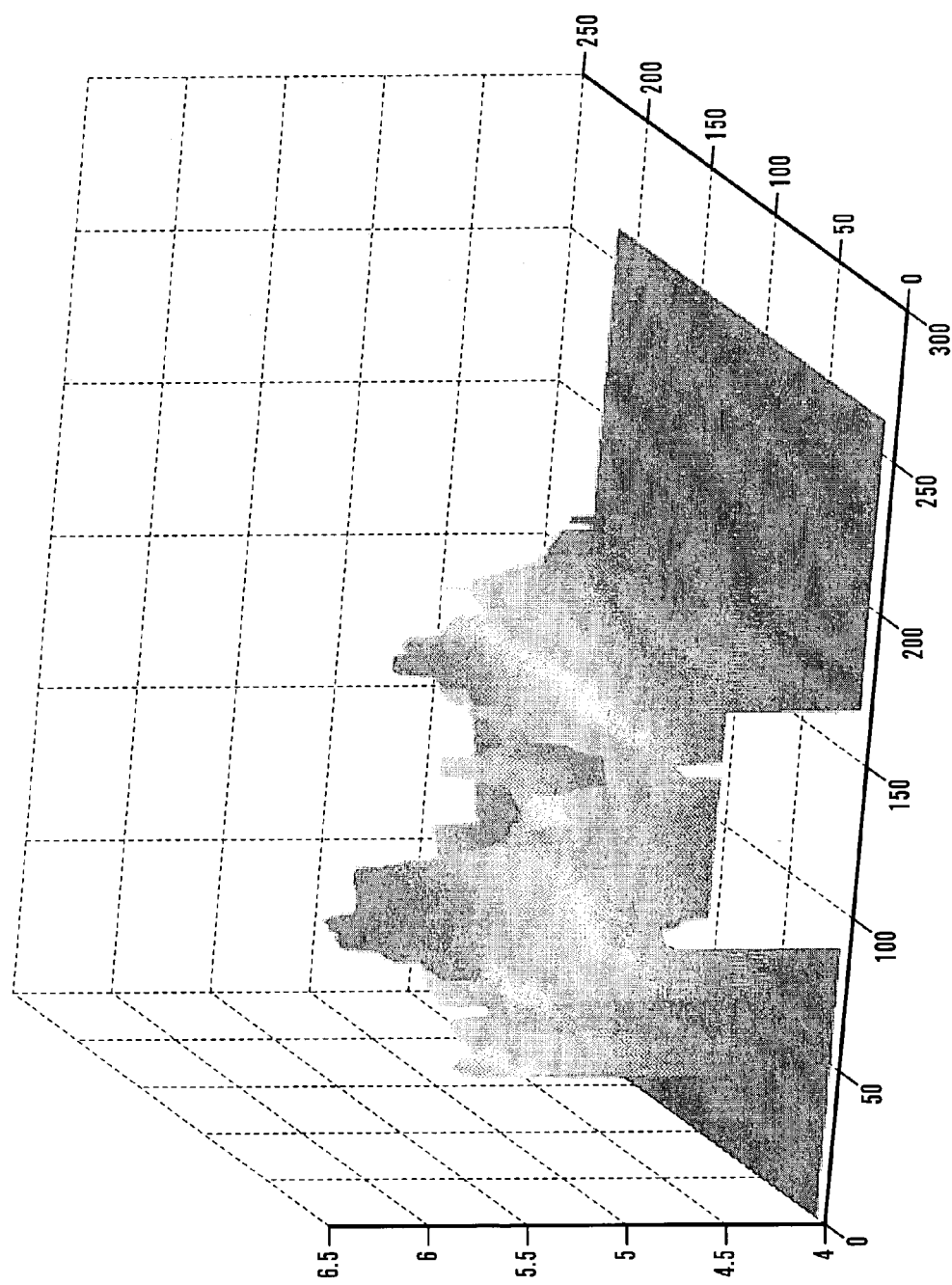
FIG. 12 is a three dimensional graph of spots of biotinylated DNA attached to a strepavidin functionalized surface after exposure to DNA complimentary.
Figure 14C:
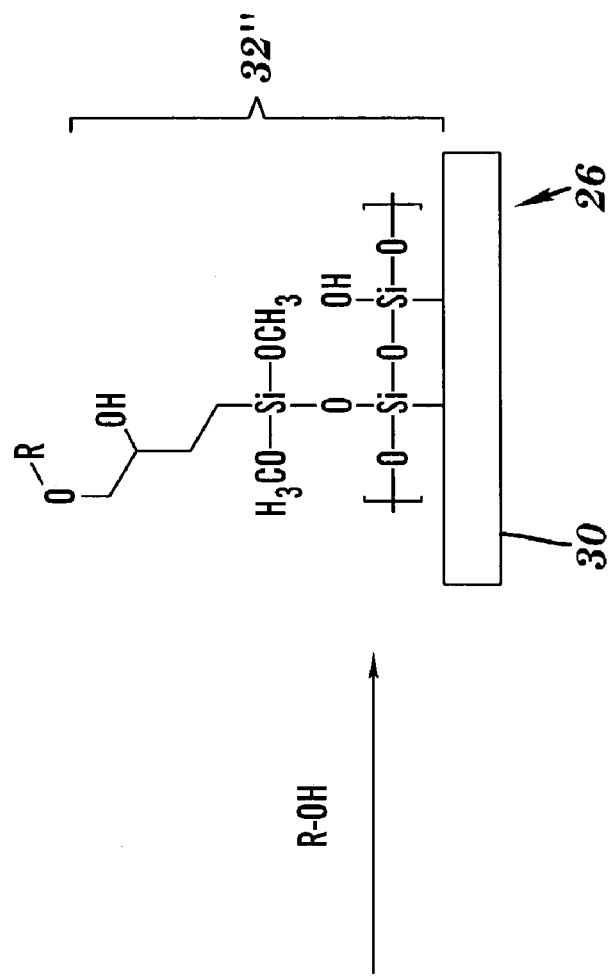
Figure 14C:
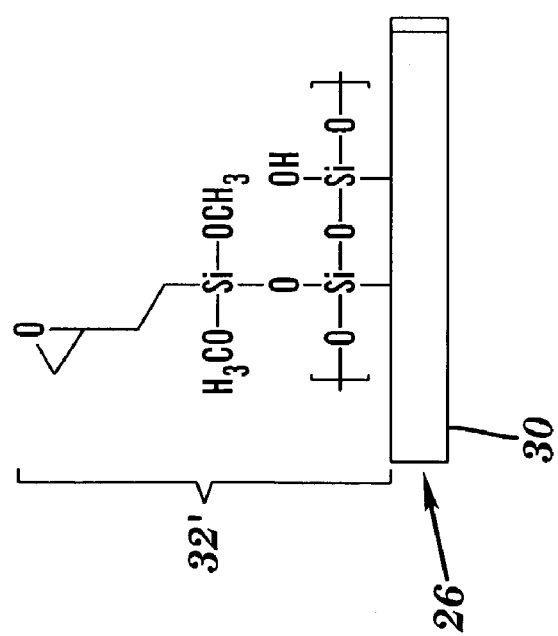
Figure 14D:
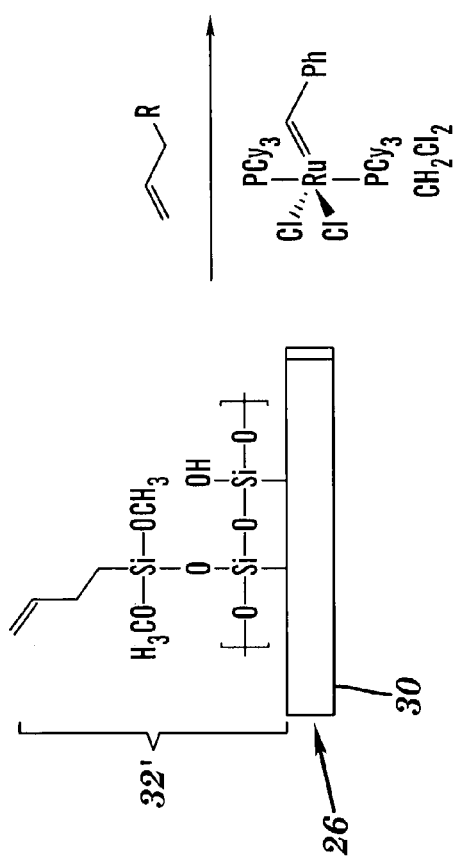
Figure 14D:
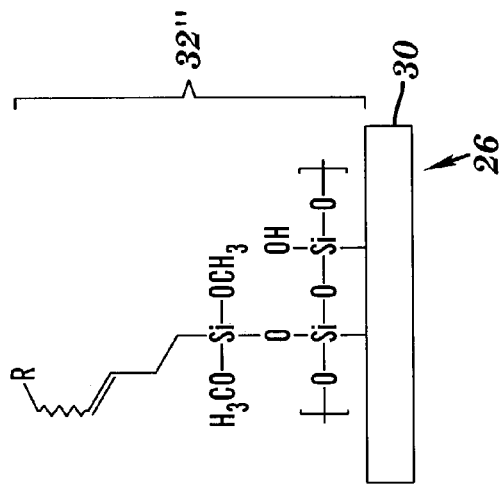
Figure 14E:
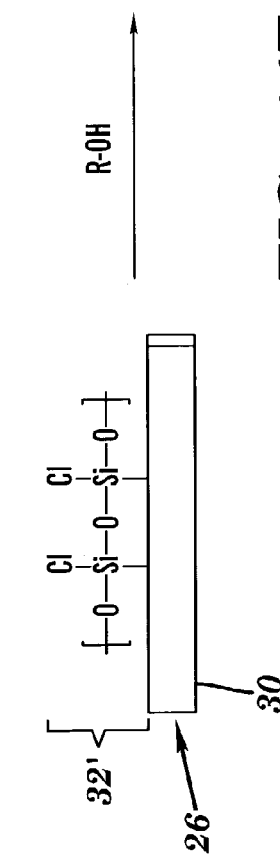
Figure 14E:
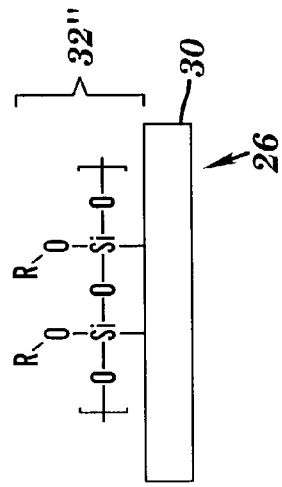

Referring to FIG. 12, the surface topology of the receptor 26 as modified after exposure to 10 picomoles (1 microliter of 10 micromolar solution) of an oligonucleotide in water with NaCl and buffer solution to allow hybridization is illustrated. The oligonucleotide is complementary to one of the biotin bound sequences. It is clear that the spot where the complement is bound grows around 0.5 nm with respect to the other or roughly 5% of a monolayer. Since it would be easy to use spots around 100 microns in size (a factor of 400 smaller) and currently changes of 0.2 nm can be detected with some confidence, it should be straightforward to detect 10 femtomoles. The system could be optimized to do at least ten times better than that as well. The present invention averts the need to do chemistry on the analyte and is easily done under aqueous analytes. It can also be implemented with a very inexpensive light source 22 and detector 28, unlike fluorescence tagging.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

What is claimed is:

1. A sensor system for sensing at least one target, the system comprising:
   a receptor for the at least one target, the receptor comprising a substrate, a translucent coating on the substrate having front and back surfaces, and one or more adsorbates attached to the front surface of the coating, said one or more adsorbates being capable of recognizing the at least one target;
   a light source positioned to direct at least a portion of s-polarized light from the light source toward the coating on the receptor at a non-normal angle of incidence that is effective to result in a condition of near perfect interference where the reflectance is less than $10^{-4}$; and
   a detector positioned to measure the light reflected from the front and back surfaces of the coating, the detector identifying presence of at least one target based on the measured reflected light.

2. The system as set forth in claim 1, wherein the light source emits non-polarized light, the system further comprising at least one s-polarizer in a path of the at least a portion of light from the light source.

3. The system as set forth in claim 2 further comprising a rotator connected to the s-polarizer.

4. The system as set forth in claim 1 wherein the substrate is silicon and the coating is silicon dioxide.

5. The system as set forth in claim 4 wherein the receptor is present in a medium of air, the angle of incidence being about 70.5 degrees.

6. The system as set forth in claim 4 wherein the receptor is present in an aqueous environment, the angle of incidence being about 85.5 degrees, the system further comprising at least one prism in a path of the at least a portion of light.

7. The system as set forth in claim 1 wherein the one or more adsorbates are selected from the group of non-polymeric small molecules, polypeptides or proteins, oligonucleotides, and combinations thereof.

8. The system as set forth in claim 1 wherein the coating further comprises a coupling agent that links the one or more adsorbates to the coating.

9. The system as set forth in claim 1 wherein a thickness of the coating is based on at least one of the angle of incidence and a wavelength of the light to result in the condition of near perfect interference.

10. The system as set forth in claim 1 wherein the light from the light source is collimated, monochromatic, or both.

11. The system as set forth in claim 1 wherein the detector captures a single polarization of the reflected light.

12. The system as set forth in claim 1 wherein the detector is an imaging array that captures an image of at least a substantial portion of the surface of the receptor.

13. The system according to claim 1 further comprising:
   a blocking agent attached to the front surface of the coating.

14. The system according to claim 13 wherein the blocking agent is an amino acid alkyl ester.

15. The system according to claim 1 wherein the condition of near perfect interference is achieved at a reflectance that is less than $10^{-5}$.

16. A method for sensing at least one target, the method comprising:
   providing a receptor for the at least one target, the receptor comprising a substrate, a translucent coating on the substrate having front and back surfaces, and one or more adsorbates attached to the front surface of the coating, said one or more adsorbates being capable of recognizing the at least one target;
   directing s-polarized light at the front and back surfaces of the coating on the receptor at a non-normal angle of incidence that is effective to result in a condition of near perfect interference where the reflectance is less than $10^{-4}$;
   measuring the s-polarized light reflected from the front and back surfaces of the coating on the receptor; and
   providing an output identifying the at least one target based on the measured reflected light.

17. The method as set forth in claim 16 further comprising rotating the polarizing of the directed light.

18. The method as set forth in claim 16 further comprising rotating the polarizing of the reflected light.

19. The method as set forth in claim 16 wherein the one or more adsorbates are selected from the group of non-polymeric small molecules, polypeptides or proteins, oligonucleotides, and combinations thereof.

20. The method as set forth in claim 16 wherein the coating further comprises a coupling agent that links the one or more adsorbates to the coating.

21. The method as set forth in claim 16 wherein a thickness of the coating is based on at least one of the angle of incidence and a wavelength of the directed light.

22. The method as set forth in claim 16 wherein the light is collimated, monochromatic, or both.

23. The method as set forth in claim 16 wherein the measuring the reflected light further comprises capturing an image of at least a substantial portion of the surface of the receptor.

24. The method according to claim 16 wherein the receptor further comprises a blocking agent attached to the front surface of the coating.

25. The method according to claim 24 wherein the blocking agent is an amino acid alkyl ester.

26. The method according to claim 16 wherein the condition of near perfect interference is achieved at a reflectance that is less than $10^{-5}$.

* * * * *